United States Patent [19]

Tacke et al.

[11] Patent Number: 5,808,136
[45] Date of Patent: Sep. 15, 1998

[54] CATALYST, METHOD OF ITS PRODUCTION AND ITS USE FOR THE PRODUCTION OF VINYL ACETATE MONOMER

[75] Inventors: Thomas Tacke, Friedrichsdorf; Herbert Mueller, Alzenau; Uwe Ohlrogge, Hanau, all of Germany; Francis P. Daly, Murray, Ky.; Hans Lansink Rotgerink, Glattbach; Helmfried Krause, Rodenbach, both of Germany

[73] Assignee: Degussa Aktiengesellschaft, Frankfurt, Germany

[21] Appl. No.: 589,256

[22] Filed: Jan. 23, 1996

[30]   Foreign Application Priority Data

Jan. 23, 1995 [DE]  Germany ................. 195 01 891.5

[51] Int. Cl.$^6$ .......................... C07C 67/055; B01J 23/38; B01J 31/04
[52] U.S. Cl. .......................... 560/243; 560/244; 560/245; 502/170; 502/243; 502/327; 502/330; 502/344; 502/349; 502/351
[58] Field of Search ................ 502/327, 330, 502/170, 243, 349, 351, 344; 560/243, 244, 245

[56]   References Cited

U.S. PATENT DOCUMENTS

| | | | |
|---|---|---|---|
| 3,761,513 | 9/1973 | Sennewald et al. | 260/497 A |
| 3,939,199 | 2/1976 | Fernholz et al. | 260/469 |
| 4,048,096 | 9/1977 | Bissot | 252/430 |
| 4,087,622 | 5/1978 | Nakamura et al. | 560/245 |
| 4,158,737 | 6/1979 | Bartsch | 560/245 |
| 4,321,409 | 3/1982 | Yoshida et al. | 560/244 |
| 4,370,292 | 1/1983 | Yanase et al. | 264/272.11 |
| 4,902,823 | 2/1990 | Wunder et al. | 560/245 |
| 5,225,388 | 7/1993 | Wunder et al. | 502/170 |
| 5,292,931 | 3/1994 | Wirtz et al. | 560/245 |
| 5,314,858 | 5/1994 | Colling | 502/330 |
| 5,332,710 | 7/1994 | Nicolau et al. | 502/243 |
| 5,347,046 | 9/1994 | White et al. | 560/245 |

FOREIGN PATENT DOCUMENTS

| | | |
|---|---|---|
| 0431478 | 6/1991 | European Pat. Off. . |
| 0634209 | 1/1995 | European Pat. Off. . |
| 1668088 | 7/1974 | Germany . |
| 3803895 | 4/1989 | Germany . |
| 3912504 | 10/1990 | Germany . |

*Primary Examiner*—Bekir L. Yildirim
*Attorney, Agent, or Firm*—Beveridge DeGrandi Weilacher & Young LLP

[57]   ABSTRACT

A catalyst and method of its production for use in making vinyl acetate monomer. The carrier is impregnated with a basic solution and a solution containing gold salts and palladium salts and finally impregnated with alkali acetate. The activity and selectivity of the catalyst, its mechanical strength, the noble-metal adhesion and the dispersion of noble metal on the carrier can be improved if the carrier is impregnated in a pretreatment with salts containing as cation elements of groups IA, IIA, IIIA and IVB of the periodic table and as anions elements of group VIIA or complex anions such as nitrate, sulfate or anions of organic acids such as acetate and lactate and is subsequently dried and calcined at temperatures of at least 160° C.

12 Claims, No Drawings

CATALYST, METHOD OF ITS PRODUCTION AND ITS USE FOR THE PRODUCTION OF VINYL ACETATE MONOMER

INTRODUCTION AND BACKGROUND

The present invention relates to a supported catalyst for the production of vinyl acetate monomer (VAM) which contains palladium, gold and alkali compounds on a support of silicon dioxide, alumosilicate or aluminum oxide as catalytically active components as well as to a method of its production and to its use.

Supported catalysts containing gold, palladium and alkali compounds are used for the production of vinyl acetate. To this end ethylene, acetic acid and molecular oxygen and/or air in the gaseous phase are brought to reaction, optionally under the addition of inert gases, at temperatures between 100° and 250° C. and customary or elevated pressure in the presence of the supported catalyst.

Such a production method is described in DE 16 68 088 and U.S. Pat. No. 4,048,996. These patents also disclose a method of producing the supported catalysts containing gold, palladium and alkali compounds. Depending on the method of manufacture, catalyst particles with homogeneous noble-metal distribution over the support cross section or with more or less pronounced shell profile are obtained.

These catalysts are usually obtained by impregnating the support particles with a basic solution and a solution containing gold- and palladium salts; the impregnations can take place simultaneously or successively with or without intermediate drying. The support particles are subsequently washed to remove any chloride components present. The noble-metal compounds precipitated on the support particles are reduced before or after the washing. The catalytic precursor obtained in this manner is dried and impregnated with alkali acetates or alkali compounds, which are converted during the production of vinyl acetate monomer entirely or partially into alkali acetates. Preferred alkali compounds are potassium compounds, especially potassium acetate.

The reduction of the catalyst can be carried out in the gas-phase or in the gaseous phase. For example, formaldehyde or hydrazine are suitable for the reduction in the gas-phase. The reduction in the gaseous phase can be carried out with hydrogen or forming gas (95% by volume $N_2$+5% by volume $H_2$) or ethylene. According to EP 0 634 209 the reduction takes place with hydrogen at temperatures between 40° and 260° C., preferably between 70° and 200° C. However, the catalyst is frequently reduced after the activation with alkali acetate directly in the production reactor with ethylene.

In the production process the catalyst is loaded only slowly with the reactants. During this startup phase the activity of the catalyst increases and usually does not reach its final level until after days or weeks.

An object of the present invention is to provide a carrier catalyst for the production of vinyl acetate monomer which catalyst exhibits a higher activity than conventional catalysts with the same or improved selectivity.

Another object of the invention is to provide a method of producing the catalyst.

SUMMARY OF THE INVENTION

The above and other objects of the invention are achieved with a supported catalyst containing palladium, gold and alkali acetate as catalytically active components on a supported of silicon dioxide, alumosilicate or aluminum oxide. The catalyst is characterized in that the support particles additionally contain at least one element from groups IA, IIA, IIIA and IVB of the periodic table of the elements.

The catalyst can be produced according to the methods known from the state of the art. The additional elements are introduced into the support particles by means of a pretreatment thereof. This pretreatment, also designated in the following as a modification, consists of an impregnation of the support particles with salts containing as cations elements of groups IA, IIA, IIIA and IVB of the periodic table and anions of group VIIA or complex anions such as nitrate, sulfate, carbonate or anions of organic acids such as acetate and lactate. Organometallic compounds, especially alcoholates, or other precursors of these elements can also be used for the impregnation. The pretreated support particles are subsequently dried and calcined at temperatures of at least 160° C.

In has proven to be advantageous to load the support particles by means of the pretreatment with said elements in an amount of 0.1 to 25% by weight relative to the weight of the support particles. It is preferable to use elements from groups IIIA and IVB of the periodic table, especially aluminum, zirconium or titanium in the form of their water-soluble salts (acetates, nitrates, chlorides). The carriers can be pretreated with individual elements or with any combinations of elements from the cited groups of the periodic table.

DETAILED DESCRIPTION OF INVENTION

According to the more detailed aspects of the invention, silicon dioxide, alumosilicates or aluminum oxide are suitable as support material for the catalyst. The silicon dioxide can be precipitated silica or even so-called pyrogenic silica obtained by the flame hydrolysis of silicon tetrachloride. It is important that the catalytic particles retain their mechanical strength under the reaction conditions of the catalytic process, especially under the influence of acetic acid. Support materials with a specific surface area greater than 10 $m^2/g$, especially a specific surface area of 50–250 $m^2/g$, are advantageous.

The catalytic supports can be present as extrudate, tablets, rings or in other forms customary for fixed-bed catalysts. The external dimensions are usually in a range between 2 and 15 mm. In the case of pyrogenic silica e.g. the supports described in DE 38 03 895 C1 and DE 39 12 504 A1 are suitable.

After the drying and calcining of the pretreated catalytic supports they are impregnated with a solution containing palladium and gold. Simultaneously with the solution containing noble metal(s) or in any successive sequence the catalytic supports are impregnated with a basic solution which can contain one or several basic compounds. The basic compound or compounds selected are those that are capable of converting the palladium and gold into their hydroxides.

The compounds in the basic solution are used in an amount sufficient to perform their intended function and include alkali hydroxides, alkali bicarbonates, alkali carbonates, alkali silicates or mixtures thereof. Potassium hydroxide and sodium hydroxide are used with preference.

In order to produce the solution containing noble metal e.g. palladium chloride, sodium- or potassium palladium chloride or palladium nitrate or mixtures thereof can be used as palladium salts. Suitable gold salts are gold(III) chloride and tetrachloroauric(III) acid. It is preferable to start from potassium palladium chloride or sodium palladium chloride and tetrachloroauric acid.

The impregnating of the support with the basic solution influences the precipitation of the noble metals in the support material. The basic solution can be brought in contact with the catalytic support either simultaneously with the noble-metal solution or in any desired sequence with this solution. In the case of successive impregnation of the support with the two solutions an intermediate drying can be carried out after the first impregnation step.

The catalytic supports are preferably impregnated with the basic compound first. The subsequent impregnation with the solution containing palladium and gold results in the precipitation of palladium and gold in a surface shell onto the catalytic supports. The inverse sequence of impregnations results in general in a more or less homogeneous distribution of the noble metals over the cross section of the catalytic supports. However, given a suitable conducting of the method, catalysts with a defined shell can be obtained even in the case of the inverse impregnating sequence (see e.g. U.S. Pat. No. 4,048,096). Catalysts with homogeneous or almost homogeneous noble-metal distribution generally exhibit a lesser activity and selectivity.

Catalysts with shell thicknesses below 1 mm, preferably approximately below 0.5 mm, are especially suitable. The shell thickness is influenced by the amount of the basic compound applied onto the support material relative to the desired amount of noble metals. The higher this ratio is, the smaller the thickness of the developing shell becomes. The mass ratio of basic compound to the noble-metal compounds which amount ratio is required for a desired shell thickness is a function of the nature of the support material as well as of the selected basic compound and noble-metal compounds. The required mass ratio is purposefully determined by a few preliminary tests. The resulting shell thickness can be determined in a simple manner by cutting open the catalytic particles.

The minimum required amount of basic compound results from the stoichiometrically calculated amount of hydroxide ions necessary for converting the palladium and gold into the hydroxides. A guideline is the fact that the basic compound must be used in a 1 to 10-fold stoichiometric excess for a shell thickness of 0.5 mm.

The catalytic supports are impregnated with the basic compounds and the noble-metal salts by pore-volume impregnation. If intermediate drying is employed the volumes of the two solutions are selected so that they correspond in each instance to approximately 90 to 100% of the absorption capacity of the support material. If intermediate drying is not employed the sum of the individual volumes of the two impregnating solutions must correspond to the above condition and the individual volumes can be in a ratio of 1:9 to 9:1 to one another. A volumetric ratio of 3:7 to 7:3, especially 1:1, is preferably used. Water is preferably used as solvent in both instances. However, suitable organic or aqueous-organic solvents can also be used.

The conversion of the noble-metal salt solution with the basic solution to insoluble noble-metal compounds takes place slowly and is generally not concluded until after 1 to 24 hours, depending on the preparation method. Thereafter the water-insoluble noble-metal compounds are treated with reducing agents. A wet reduction e.g. with aqueous hydrazine hydrate or a gas-phase reduction with hydrogen, ethylene or also methanol vapors can be carried out. The reduction can take place at normal temperature or elevated temperature and at normal pressure or elevated pressure. It is preferable to use a wet reduction with aqueous hydrazine hydrate or a gas-phase reduction with forming gas.

The chloride optionally present on the support is removed by a thorough washing before or after the reduction of the noble-metal compounds. After the washing the catalyst should contain less than 500, preferably, less than 200 ppm chloride.

The catalytic precursor obtained after the reduction is dried and finally impregnated with alkali acetates or alkali compounds which are converted entirely or partially into alkali acetates under the reaction conditions during the production of vinyl acetate monomer. Potassium acetate is preferably used for the impregnation. Pore-volume impregnation is again preferably used for this, that is, the required amount of potassium acetate is dissolved in a solvent, preferably water, whose volume corresponds approximately to the absorption capacity of the support material used for the selected solvent. This volume is approximately equal to the total pore volume of the support material.

The finished catalyst is subsequently dried until a residual moisture of less than 2%. The drying can take place in air, optionally also under nitrogen as inert gas.

It is advantageous for the synthesis of vinyl acetate monomer to impregnate the catalyst with 0.3 to 4, preferably 0.5 to 3% by weight palladium, 0.1 to 2, preferably 0.2 to 1.5% by weight gold and 1 to 10, preferably 3.5 to 10% by weight potassium acetate relative in each instance to the weight of the support used. In the case of catalytic supports with a bulk density of 500 g/l these indications of concentration correspond to volume-related concentrations of 1.5 to 20 g/l palladium, 0.5 to 10 g/l gold and 5 to 50 g/l potassium acetate. For preparation of the impregnating solutions the correspondingly appropriate amounts of the palladium compounds and gold compounds are dissolved in a volume of water corresponding to approximately 90 to 100% of the water adsorption capacity of the support material used. The same procedure is used for the preparation of the basic solution.

Pore-volume impregnation is also used for the pretreatment in accordance with the invention of the catalytic supports with the specified cations. The catalytic supports are thereafter dried at elevated temperatures and calcined at temperatures of 160° to 800°, preferably 170° to 700° C.

The catalysts applied onto pretreated supports exhibit a greater activity in the production of vinyl acetate than conventional catalysts do. In addition, an improved noble-metal adhesion is observed in the case of the pretreated catalysts. If non-pretreated catalytic supports are used, noble-metal losses occur when the chlorides are washed out after the reduction of the noble-metal compounds. These losses are typically about 10% for gold and about 6% for palladium. In contrast thereto the gold losses drop to about 6% and the palladium losses to only about 3% if the catalytic carriers are pretreated in accordance with the invention. Surprisingly, the increased individual mass particle strength is also observed in the case of the catalysts in accordance with the invention. It is approximately 70N for the supported catalysts of the invention (example 2) and 78N (example 1), whereas the conventionally produced supported catalysts have an individual particle strength of only about 48N (comparative example 1).

Even the dispersion of noble metals is improved in the case of the catalysts of the invention. Thus, e.g. in the case of the catalysts of the invention a CO value (CO adsorption by means of CO pulse chemisorption) a measure for the noble-metal dispersion is 0.186 ml CO/g catalyst (example 1) whereas the CO value for conventional catalysts is only approximately 0.158 ml CO/g catalyst (comparative example 1). The cause for the improved dispersion of the catalytically active noble metals could be the observation that the specific surface area of the catalytic support treated in accordance with the invention does not decrease due to the impregnation with the basic solution, especially with sodium hydroxide solution or potash lye. On the other hand, non-pretreated support exhibits a reduction of the specific surface area which is drastic in some instances upon the action of the basic solution. This is associated with a corresponding lowering of the noble-metal dispersion of the catalysts.

A further advantageous embodiment of the invention is obtained if the catalyst is reduced in the gas phase with hydrogen-containing gas at elevated temperatures. The gas-phase reduction of catalysts for the synthesis of vinyl acetate monomer is already known. However, it is carried out at relatively low temperatures. Thus, e.g. U.S. Pat No. 4,370,292 prescribes a reduction at temperatures between 40° and 260°, preferably between 70° and 200° C.

It surprisingly turned out that catalysts reduced in a temperature range between 300° and 550°, preferably between 350° and 500° C., with forming gas exhibit distinctly greater activities for the synthesis of vinyl acetate monomer with simultaneously increased selectivity. This is also especially applicable to catalysts whose supports were not pretreated with elements.

COMPARATIVE EXAMPLE 1

A conventional palladium-gold-potassium acetate catalyst on an alumosilicate support KA 160 of Südchemie was produced. The support particles are spherical with a diameter of approximately 5 mm and have a specific surface area of 160 to 175 m$^2$/g, a bulk density of 600 g/l and a total pore volume of 0.68 cm$^3$/g. The concentrations of the impregnating solutions were selected in such a manner that the finished catalyst contained 3.3 g palladium, 1.5 g gold and 30 g potassium acetate per liter bulk volume of the catalytic support, which corresponded to a concentration of 0.55% by weight palladium, 0.25% by weight gold and 5% by weight potassium acetate relative to the weight of the support used.

In a first step the support were at first impregnated with a solution of potassium hydroxide. The concentration of the solution of potassium hydroxide was calculated so that after the impregnation a stoichiometric excess of potassium hydroxide on the support of 620% was present.

After the drying of the catalytic supports they were impregnated with an aqueous solution of tetrachloroauric acid and potassium palladium chloride. After 20 hours the insoluble noble-metal compounds were reduced in the aqueous phase with hydrazine hydrate for a period of 4 hours. Then the catalytic supports were washed free of chloride and dried before they were impregnated with a potassium acetate solution and redried. Before the impregnation with potassium acetate the specific surface area of the catalyst according to DIN 66 132 was 60–70 m$^2$/g. Due to the impregnation and activation with potassium acetate the specific surface area of the catalyst declined further to 41 m$^2$/g.

The CO adsorption of the catalyst before the activation was approximately 0.158 ml CO/g catalyst. The particle crush strength of the activated catalyst was 48N (in radial measuring). The thickness of its outer shell containing noble metal was 0.3 mm.

EXAMPLE 1

A palladium-gold-potassium acetate catalyst was produced as described in comparative example 1. However, the catalytic supports were impregnated beforehand with aluminum chloride. The alumosilicate support KA 160 of Südchemie was again used as catalytic support.

To this end an aqueous solution of aluminum chloride hydrate was prepared whose concentration was calculated so that 0.11 mole aluminum chloride hydrate per 200 g support material was present. After this impregnation step the catalytic carriers were dried and calcined at 150°–180° C. for 2 hours.

Before the impregnation with potassium acetate the specific surface area of the catalyst was still 140–150 m$^2$/g. Due to the activation with potassium acetate the specific surface area of the catalyst declined to 94 m$^2$/g.

The CO adsorption of the catalyst before the activation was 0.186 ml CO/g catalyst. The crush strength of the activated catalyst was 78N. Its noble-metal-containing outer shell had a thickness of 0.3 mm.

EXAMPLE 2

A palladium-gold-potassium acetate catalyst was produced as described in comparative example 1. However, the catalytic support was impregnated beforehand in accordance with the invention with zirconium acetate. The alumosilicate support KA 160 of Südchemie was used as catalytic support.

An aqueous solution of zirconium acetate was prepared whose concentration was calculated so that 0.11 mole zirconium acetate per 200 g support material was present. After this impregnation step the catalytic support was dried and calcined at 150°–180° C. for 2 hours. Otherwise, the catalyst was produced as described in comparative example 1.

Before the impregnation with potassium acetate the specific surface area of the catalyst was still 140 m$^2$/g. Due to the impregnation with potassium acetate the specific surface area of the catalyst declined to 94 m$^2$/g.

The CO adsorption of the catalyst before the activation was approximately 0.186 ml CO/g catalyst. The crush strength of the activated catalyst was 70N. Its noble-metal-containing outer shell had a thickness of 0.3 mm.

COMPARATIVE EXAMPLE 2

A conventional palladium-gold-potassium acetate catalyst was produced analogously with comparative example 1 on a catalytic support of pyrogenic silica (AEROSIL-support 350 of Degussa; specific surface area 180 m$^2$/g; bulk density 490 g/l; total pore volume 0.8 cm$^3$/g; tablets 6 mm in diameter and 5.5 mm high). The concentration of the impregnation solutions was selected so that the finished catalyst contained 2.71 g palladium, 1.23 g gold and 24.6 g potassium acetate per liter bulk volume of the catalytic support. This corresponded to a concentration of 0.55% by weight Pd, 0.25% by weight Au and 5.0% by weight potassium acetate relative to the weight of the support material used. Otherwise, the catalyst was produced as described in comparative example 1.

The CO adsorption of the catalyst before the activation was 0.144 ml CO/g catalyst. Its shell thickness was determined at 0.5 mm.

EXAMPLE 3

A palladium-gold-potassium acetate catalyst was produced as described in comparative example 2. However, the catalytic support was impregnated beforehand in accordance with the invention with aluminum chloride hydrate. The impregnation with aluminum chloride hydrate was carried out as described in example 1. The support of comparative example 2 produced from pyrogenic silica was used as catalytic support.

The CO adsorption of the catalyst before the activation with potassium acetate was approximately 0.314 ml CO/g catalyst.

CATALYTIC ACTIVITY EXAMPLE 1

Activity and selectivity of the catalysts of the preceding examples were measured during a long-time test for up to 200 hours. The activity of the catalysts increases continuously during initial phase which can be several hours or days and reaches a constant value only after the conclusion of this phase. The measured values indicated in table 1 were obtained only after the conclusion of the particular forming phase.

The catalysts of comparative examples 1 and 2 as well as of examples 1 to 3 were tested in an oil-heated tubular-flow reactor (reactor length 800 mm, inner diameter 24.8 mm) at normal pressure and a space velocity (GHSV=gas hourly space velocity) of 400 h$^{-1}$ with the following gas composition: 76.0% by volume ethylene, 18.0% by volume acetic acid, 6.0% by volume oxygen.

Depending on the activity and the selectivity of the catalysts, the reactor temperature was adjusted so that the temperature in the middle of the catalytic bed was between 150° and 160° C.

The reaction products were condensed in the reactor outlet and investigated as to their composition with gas chromatography. The space-time yield of the catalyst was determined in grams vinyl acetate monomer per hour and liter catalytic volume (g VAM/(h·l$_{cat}$)) and in grams vinyl acetate monomer per hour and kilogram catalyst (g VAM/h·kg$_{cat}$)) as measure for the catalytic activity. Carbon dioxide, which is formed especially by the combustion of ethylene, was measured in the exhaust gas of the reactor and used to evaluate the catalytic selectivity.

Table 1 shows the test results of catalysts B1, B2 and B3 produced on the pretreated catalytic support in comparison to the catalysts (comparative catalysts) VB1 and VB2 produced on the non-pretreated catalytic support.

TABLE 1

| Catalyst | Activity $\frac{\text{g VAM}}{\text{h} \cdot \text{l}_{cat}}$ | Activity $\frac{\text{g VAM}}{\text{h} \cdot \text{kg}_{cat}}$ | CO$_2$ Ex. gas [Vol-%] | Catalyst-temperature [°C.] |
|---|---|---|---|---|
| VB 1 | 49.2 | 76.2 | 1.1 | 159 |
| B 1 | 64.7 | 100.3 | 1.7 | 155 |
| B 2 | 53.7 | 83.3 | 1.5 | 155 |
| VB 2 | 48.4 | 98.3 | 1.2 | 155 |
| B 3 | 58.8 | 119.3 | 1.4 | 152 |

The examples show that the catalysts of the invention make possible a clearly increased space-time yield of vinyl acetate monomer with comparable formation of CO$_2$.

The catalyst on the support of modified pyrogenic silica (example 3) displays a clearly higher space-time yield relative to weight than the catalysts on the support of modified alumosilicate KA 160 (examples 1 and 2). The catalyst according to example 3 is, moreover, more selective than the corresponding catalyst according to example 1.

COMPARATIVE EXAMPLE 3

A conventional palladium-gold-potassium acetate catalyst was produced on alumosilicate support KA 160. The concentration of the impregnation solutions was selected so that the finished catalyst contained 3.3 g palladium, 1.5 g gold and 30 g potassium acetate per liter bulk volume of the catalytic support. This corresponded to a concentration of 0.55% by weight palladium, 0.25% by weight gold and 5.0% by weight potassium acetate relative to the weight of the support used.

In a first step the support was impregnated at first with a basic solution of sodium hydroxide in water. The volume of the aqueous NaOH solution corresponded to 50% of the water absorption of the dry support. After the impregnation with sodium hydroxide the support was impregnated immediately without intermediate drying with an aqueous noble-metal solution of sodium palladium chloride and tetrachloroauric acid whose volume likewise corresponded to 50% of the water absorption capacity of the dry support material.

After a waiting time of 1.5 hours for hydrolysis of the noble-metal compounds the support particles were washed free of chlorine.

The catalyst was dried and reduced with forming gas at 150° C. in the gas phase as described in EP 0,634,209. Then the catalyst was impregnated with an aqueous potassium acetate solution and redried. The drying was carried out in the gas phase with nitrogen.

The concentration of the basic solution of sodium hydroxide was calculated so that a noble-metal-containing shell 0.3 mm thick formed on the support particles.

COMPARATIVE EXAMPLE 4

A palladium-gold-potassium acetate catalyst was produced as described in comparative example 3. The alumosilicate support KA 160 was used as catalytic support. However, in distinction to comparative example 3 the catalyst was not reduced with forming gas in the gas phase but rather in aqueous phase with hydrazine.

COMPARATIVE EXAMPLE 5

A palladium-gold-potassium acetate catalyst was produced as described in comparative example 3. The alumosilicate support KA 160 was used as catalytic support. However, in distinction to comparative example 3 the catalyst was not reduced with forming gas but rather with ethylene in the gas phase at 150° C.

EXAMPLE 4

A palladium-gold-potassium acetate catalyst was produced as described in comparative example 3. The alumosilicate support KA 160 was used as catalytic support. However, in distinction to comparative example 3 the catalyst was not reduced at 150° C. but rather at 450° C. in the gas phase with forming gas.

CATALYTIC ACTIVITY EXAMPLE 2

Activity and selectivity of the catalysts of comparative examples 3, 4 and 5 and of example 4 were measured in a test lasting up to 24 hours.

The catalysts were tested in an oil-heated tubular-flow reactor (reactor length 710 mm, inner diameter 23.7 mm) at normal pressure and a space velocity (GHSV) of 400 h$^{-1}$ with the following gas composition: 75% by volume ethylene, 16.6% by volume acetic acid, 8.3% by volume oxygen. The catalysts were tested in a temperature range of 120° to 165° C., measured in the catalytic bed.

The reaction products were analyzed in the reactor outlet by means of on-line gas chromatography. The space-time yield of the catalyst was determined in grams vinyl acetate monomer per hour and liter catalytic volume (g VAM/(h·$l_{cat}$)) and in grams vinyl acetate monomer per hour and kilogram catalyst (g VAM/h·$kg_{cat}$)) as measure for the catalytic activity. Carbon dioxide, which is formed especially by the combustion of ethylene, was likewise determined and used to evaluate the catalytic selectivity.

Table 2 shows the test results of catalysts from comparative examples 3, 4 and 5 as well as of example 4.

TABLE 2

| Catalyst | Activity $\frac{g\ VAM}{h \cdot l_{cat}}$ | Activity $\frac{g\ VAM}{h \cdot kg_{cat}}$ | $CO_2$ Ex. gas [Vol.-%] | Catalyst temperature [°C.] |
|---|---|---|---|---|
| VB 3 | 24.5 | 38.0 | 0.81 | 156 |
| VB 4 | 57.2 | 88.6 | 3.76 | 155 |
| VB 5 | 94.7 | 146.8 | 4.44 | 155 |
| B 4 | 108.8 | 168.5 | 3.33 | 153 |

Example 4 shows that the catalyst reduced at 450° C. with forming gas makes possible a clearly increased space-time yield of vinyl acetate monomer.

If the catalyst is reduced as described in comparative example 3 at 150° C. with forming gas in the gas phase only a very low space-time yield of vinyl acetate monomer results. The reduction in liquid phase with hydrazine (comparative example 4) or with ethylene in the gas phase at 150° C. (comparative example 5) results in catalysts with a clearly improved space-time yield of vinyl acetate monomer. If the catalyst is now reduced as described in example 4 at 450° C. in the gas phase with forming gas the space-time yield of vinyl acetate monomer can surprisingly be clearly increased again. In comparison to the less selective catalysts of comparative examples 4, 5 even the selectivity was able to be clearly increased.

COMPARATIVE EXAMPLE 6

A palladium-gold-potassium acetate catalyst on alumosilicate support KA 160 was produced as described in example 4. However, the catalytic support was impregnated beforehand with lanthanum nitrate.

For this, an aqueous solution of lanthanum nitrate was prepared whose concentration was calculated so that 0.11 mole lanthanum nitrate per 200 g carrier material was present. After this impregnation step the catalytic support was dried and calcined at 150°–180° C. for 2 hours.

COMPARATIVE EXAMPLE 7

A palladium-gold-potassium acetate catalyst on alumosilicate support KA 160 was produced as described in comparative example 6. The catalytic support was pretreated with bismuth chloride instead of with lanthanum nitrate.

EXAMPLE 5

A palladium-gold-potassium acetate catalyst on alumosilicate support KA 160 was produced as described in comparative example 6. The catalytic support was pretreated with titanium(III) chloride instead of with lanthanum nitrate.

EXAMPLE 6

A palladium-gold-potassium acetate catalyst on alumosilicate support KA 160 was produced as described in comparative example 6. The catalytic support was pretreated with zirconium acetate instead of with lanthanum nitrate.

The catalysts of examples B4 to B6 and of comparative examples VB6 and VB7 were tested for activity and selectivity as described in catalytic activity example 2. The test results are collated in table 3.

TABLE 3

| Catalyst | Activity $\frac{g\ VAM}{h \cdot l_{cat}}$ | Activity $\frac{g\ VAM}{h \cdot kg_{cat}}$ | $CO_2$ Ex. gas [area-%] | Catalyst-temperature [°C.] |
|---|---|---|---|---|
| B 4 | 108.8 | 168.6 | 3.33 | 153 |
| VB 6 | 53.7 | 83.2 | 1.41 | 147 |
| VB 7 | 65.9 | 102.1 | 1.04 | 145 |
| B 5 | 109.1 | 169.1 | 2.60 | 155 |
| B 6 | 111.5 | 172.8 | 2.04 | 139 |

Table 3 shows the catalyst temperatures at which each catalyst yielded the highest space-time yield.

The catalysts of comparative example 6 (lanthanum-modified catalytic support) and of comparative example 7 (bismuth-modified catalytic support) display considerably poorer performance data than the catalysts of examples B4 to B6. The catalysts of example 5 (titanium-modified catalytic support) and of example 6 (zirconium-modified catalytic support) are still somewhat more active and more selective than the catalysts of example 4 on the non-modified catalytic support. The catalysts of example 6 (zirconium-modified catalytic support) yield the highest space-time yield at a comparatively very low temperature of 139° C.

EXAMPLE 7

A palladium-gold-potassium acetate catalyst on alumosilicate support KA 160 was produced according to example 4.

However, in distinction to the catalyst of example 4 the catalyst in the present instance was produced with a noble-metal content of 1.2% by weight palladium, 0.5% by weight gold and 5% by weight potassium acetate.

EXAMPLE 8

A palladium-gold-potassium acetate catalyst on alumosilicate support KA 160 was produced according to example 4.

However, in distinction to the catalyst of example 4 the catalyst in the present instance was produced with a noble-metal content of 1.2% by weight palladium, 0.5% by weight gold and 5% by weight potassium acetate. In addition, the catalytic supportwas impregnated before the coating with noble metal with zirconium acetate as described in example 2.

EXAMPLE 9

A palladium-gold-potassium acetate catalyst on alumosilicate support KA 160 was produced according to example 8.

In deviation from example 8 the catalytic support was pretreated with aluminum chloride hydrate as described in example 1.

Table 4 shows the test results of the catalysts produced on the pretreated or modified catalytic supports in comparison to the catalyst of example 7 produced on the non-pretreated catalytic supports. The catalysts were tested as described in catalytic activity example 2.

TABLE 4

| Catalyst | Activity $\frac{g\ VAM}{h \cdot l_{cat}}$ | Activity $\frac{g\ VAM}{h \cdot kg_{cat}}$ | $CO_2$ Ex. gas [area-%] | Catalyst-temperature [°C.] |
|---|---|---|---|---|
| B 7 | 122.5 | 189.9 | 3.3 | 144 |
| B 8 | 129.0 | 200.0 | 3.3 | 143 |
| B 9 | 135.7 | 210.3 | 3.5 | 148 |
|  | 145.5 | 225.5 | 5.6 | 155 |

Even examples 8 and 9 show that catalysts on modified catalytic supports display a clearly increased space-time yield at comparable selectivity.

EXAMPLE 10

A palladium-gold-potassium acetate catalyst was produced according to example 4. A support of pyrogenic silica like in comparative example 2 was used as catalytic support. In distinction to the catalyst of example 4 the catalyst in this instance was produced with a noble-metal content of 1.2% by weight palladium, 0.5% by weight gold and 5% by weight potassium acetate.

EXAMPLE 11

A palladium-gold-potassium acetate catalyst was produced according to example 10.

In distinction to example 10 the catalytic support was impregnated with zirconium acetate as in example 2 before the coating with noble metal.

EXAMPLE 12

A palladium-gold-potassium acetate catalyst was produced according to example 11.

In distinction to the catalyst of example 11 the support was not dried and calcined at 150° to 180° C. after the pretreatment with zirconium acetate but rather was first dried at 120° C. and then calcined at 400° C. for a period of 1 to 2 hours.

Table 5 shows the test results of the catalysts produced on the pretreated catalytic supports in comparison to the catalyst of example 10 produced on the non-pretreated catalytic support. The catalysts were tested as described in catalytic activity example 2.

TABLE 5

| Catalyst | Activity $\frac{g\ VAM}{h \cdot l_{cat}}$ | Activity $\frac{g\ VAM}{h \cdot kg_{cat}}$ | $CO_2$ Ex. gas [area-%] | Catalyst-temperature [°C.] |
|---|---|---|---|---|
| B 10 | 83.2 | 168.9 | 2.00 | 135 |
| B 11 | 103.9 | 210.9 | 1.93 | 143 |
| B 12 | 107.8 | 218.8 | 1.81 | 132 |

The catalyst test results in table 5 show that the catalysts of examples 11 and 12 on modified catalytic support display both a clearly higher activity and also a lower formation of $CO_2$ and therewith a higher selectivity in comparison to the catalyst of example 10 on a non-modified catalytic support.

EXAMPLE 13

In the following examples AEROSIL support 350 of Degussa (see comparative example 2) was modified by being impregnated with various titanium compounds and zirconium compounds.

For the modification of 100 g support with 1.5% by weight titanium 33 g of a 15% titanium chloride solution ($TiCl_3$) were diluted with water to 80 ml, corresponding to the pore volume of the support material. The support material was impregnated with this solution.

After 30 minutes exposure time the support was dried at 100° C. for 3 hours in a drying oven and then calcined in an oven at 600° C. for 4 hours.

EXAMPLE 14

For the modification of 100 g support with 4% by weight titanium 85.93 g of a 15% titanium chloride solution were diluted with water to 80 ml and distributed over the support for its impregnation.

After 30 minutes exposure time the support was dried at 100° C. for 3 hours in a drying oven and then calcined in an oven at 600° C. for 4 hours.

EXAMPLE 15

For the modification of 100 g support with 5% by weight titanium 35.5 g tetrabutoxytitanium ($Ti(C_4H_9O)_4$) were diluted with butanol to 80 ml and distributed over the support.

After 30 minutes exposure time the support was dried at 100° C. for 3 hours in a drying oven and then calcined in an oven at 600° C. for 4 hours.

EXAMPLE 16

For the modification of 100 g support with 5% by weight zirconium 21.03 g tetrabutoxyzirconium (IV) were diluted with butanol to 80 ml and distributed over the support.

After 30 minutes exposure time the support was dried at 100° C. for 3 hours in a drying oven and then calcined in an oven at 600° C. for 4 hours.

EXAMPLE 17

For the modification of 100 g support with 8% by weight zirconium 28.23 g zirconyl chloride ($ZrOCl_2 \cdot 8H_2O$) were dissolved in 62.37 g water and distributed over the support.

After 30 minutes exposure time the support was dried overnight at 120° C. in a drying oven and then calcined in the oven at 500° C. for 3 hours.

The crush strength of the support particles before the modification was 101N (radial measurement). After the modification with 8% by weight zirconium the crush strength was 140N.

EXAMPLE 18

100 g support were modified with 8% by weight zirconium as in example 17. In order to investigate the influence of the calcining temperature on the compressive strength of the support particles one third of the support particles was calcined 3 hours at 200, another third 3 hours at 400 and the last third 3 hours at 600° C.

The crush strength of these support particles was 123N (calcining at 200° C.), 153N (calcining at 400° C.) and 148N (calcining at 600° C.).

EXAMPLE 19

The zirconium content of the support of example 17 is to be raised further by another impregnation. To this end 8.9 g zirconyl chloride ($ZrOCl_2 \cdot 8H_2O$) were dissolved in 7.23 g water and 14.95 g of the support impregnated therewith. This raised the zirconium content of the support to 21.1% by weight.

After 30 minutes exposure time the support was dried overnight at 120° C. in a drying oven and then calcined in the oven at 500° C. for 3 hours.

The crush strength of the support particles modified with 21.1% by weight was 163N.

Further variations and modifications will become apparent to those skilled in the art from the foregoing and are intended to be encompassed by the claims appended hereto.

German priority application 195 01 891.5 is relied on and incorporated herein by reference.

We claim:

1. A supported catalyst for the production of vinyl acetate monomer comprising
   a support of silicon oxide, alumosilicate or aluminum oxide, and which support additionally is impregnated with at least one element from a member of the group consisting of titanium and zirconium and a catalytically active component comprising palladium, gold and alkali acetate.

2. The supported catalyst according to claim 1, wherein the additional elements are present in a concentration of 0.1 to 25% by weight relative to the weight of the support.

3. A method of producing a supported catalyst for the production of vinyl acetate monomer comprising:
   pretreating the support by impregnating the support with a salt containing as a cation at least one element selected from the group consisting of titanium and zirconium and an anion selected from the group consisting of a group VIIA anion, a complex anion, an anion of an organic acid or an anion of an organometallic compound,
   drying the support at elevated temperatures and subsequently
   calcining the support at a temperature of from 160° to 800° C.,
   impregnating the support with a basic solution and a solution containing a gold salt and a palladium salt, to precipitate an insoluble compound on the support wherein said impregnating with said basic solution and said gold salt solution takes place simultaneously or successively with or without intermediate drying,
   washing said support to remove any chloride components present and
   reducing the insoluble compound precipitated on the support before or after the washing step to form a catalytic precursor,
   drying the catalytic precursor obtained thereby, and
   impregnating said support with an alkali acetate or alkali compound.

4. The method according to claim 3 wherein the element(s) of the pretreatment step are impregnated into the support in an amount of 0.1 to 25% by weight relative to the weight of the support.

5. The method according to claim 3 wherein the reduction is carried out in forming gas at temperatures between 300° and 550° C.

6. The method according to claim 3 wherein the reduction is carried out in forming gas at temperatures between 350° and 500° C.

7. A method of producing a supported catalyst for the production of vinyl acetate monomer containing on a support of silicon dioxide, alumosilicate or aluminum oxide, paladium, gold and alkali acetate as catalytically active components, comprising
   impregnating the support with a basic solution, and with a solution containing a gold salt and a palladium salt to precipitate an insoluble compound on the support, wherein said impregnating with said basic solution and said gold salt solution takes place simultaneously or successively with or without intermediate drying,
   washing the support to remove any chloride components present,
   reducing the insoluble compound precipitated on the support before or after the washing step to form a catalytic precursor wherein the reduction is carried out in forming gas at a temperature between 300° and 550°,
   drying the catalytic precursor obtained thereby, and
   impregnating with an alkali acetate or an alkali compound.

8. The method according to claim 7 wherein the temperature is from 350° to 500°.

9. A supported catalyst produced by the method of claim 7.

10. A method for the production of vinyl acetate monomer comprising reacting ethylene, acetic acid and oxygen on the catalyst according to claim 1 in the gas phase at ambient or elevated pressure.

11. A method of producing a supported catalyst for the production of vinyl acetate monomer comprising:
   pretreating the support by impregnating the support with a salt containing as a cation at least one element selected from the group consisting of group IA, IIA, IIIA and IVB of the periodic table and an anion selected from the group consisting of a group VIIA anion, a complex anion, an anion of an organic acid or an anion of an organometallic compound,
   drying the support at elevated temperatures and subsequently
   calcining the support at a temperature of from 160° to 800° C.,
   impregnating the support with a basic solution, and with a solution containing a gold salt and a palladium salt to precipitate an insoluble compound on the support, wherein said impregnating with said basic solution and said gold salt solution takes place simultaneously or successively with or without intermediate drying,
   washing said support to remove any chloride components present and
   reducing the insoluble compound precipitated on the support before or after the washing step to form a catalytic precursor wherein the reduction is carried out in forming gas at a temperature between 300° and 550°,
   drying the catalytic precursor obtained thereby, and
   impregnating said support with an alkali acetate or alkali compound.

12. A supported catalyst produced by the method of claim 8.

* * * * *